United States Patent [19]

Mak et al.

[11] Patent Number: 4,720,490

[45] Date of Patent: * Jan. 19, 1988

[54] FLUORALKYLATEDCARBAPENEM DERIVATIVES

[75] Inventors: Ching P. Mak; Hans Fliri, both of Vienna, Austria

[73] Assignee: Sandoz Ltd., Tokyo, Japan

[*] Notice: The portion of the term of this patent subsequent to Jan. 19, 2005 has been disclaimed.

[21] Appl. No.: 793,011

[22] Filed: Oct. 30, 1985

Related U.S. Application Data

[63] Continuation of Ser. No. 517,513, Jul. 26, 1983, abandoned.

[30] Foreign Application Priority Data

Jul. 26, 1982 [CH] Switzerland ............................ 4539/82
Sep. 24, 1982 [CH] Switzerland ............................ 5654/82
Dec. 31, 1982 [CH] Switzerland ............................ 7648/82

[51] Int. Cl.$^4$ .................... C07D 487/04; A61K 31/40
[52] U.S. Cl. .................................... 514/210; 540/350

[58] Field of Search ............... 260/245.2 R, 245.2 T; 540/350

[56] References Cited

U.S. PATENT DOCUMENTS 4,372,965  2/1983  Christensen et al. ........ 260/245.2 T
4,413,000  11/1983  Eglington .................... 260/245.2 T
4,477,662  10/1984  Corbett et al. ............... 260/245.2 T

OTHER PUBLICATIONS

Mak, (Amer. Med. Chem. Symposium), Toronto, Canada, Jun. 1982.

*Primary Examiner*—Nicholas S. Rizzo
*Attorney, Agent, or Firm*—Robbins & Laramie

[57] ABSTRACT 6-(1'-fluorethyl)- and 6-(1'-fluoro-1'-methylethyl)-carbapenems such as (5RS,6RS)-1-aza-6-(1(RS)-fluorethyl)-3-(N'-dimethyl-N'-methylamidinomethylthio)-7-oxobicyclo[3.2.0]hept-2-ene-2-carboxylic acid which are useful as chemotherapeutic agents in particular as anti-bacterially active anti-biotics.

6 Claims, No Drawings

FLUORALKYLATEDCARBAPENEM DERIVATIVES

This is a continuation of application Ser. No. 517,513, filed July 26, 1983 now abandoned.

The present invention concerns 6-(1'-fluorethyl)- and 6-(1'-fluoro-1'-methylethyl)-carbapenems, processes for their production and their use as chemotherapeutics.

No. EPA1628 discloses a very wide range of carbapenem derivatives having antibiotic activity but makes no mention of the fluoralkylated compounds of the present invention and their advantageous antibiotic properties.

More particularly the invention concerns compounds of formula I

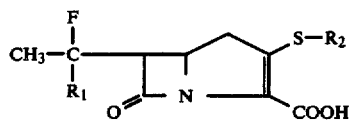

wherein,
$R_1$ represents hydrogen or methyl and
$R_2$ represents hydrogen or lower alkyl, lower alkenyl or cycloalkyl each of which may be unsubstituted or mono- or poly-substituted by amino, mono- or di-(lower)-alkylamino, lower acylamino, carboxy, lower alkoxycarbonyl or carbamoyl;
a group of formula IIc $$(CH_2)_p\text{—}R_7 \qquad IIc$$

wherein $R_7$ represents phenyl or a 5- or 6-membered saturated or unsaturated heterocycle containing one or more heteroatoms selected from O, S and/or N and which may be unsubstituted or mono- or poly-substituted by fluoro, chloro, bromo, amino, mono- or di-(lower)-alkylamino, hydroxy, lower alkoxy, mercapto, alkylthio, phenylthio, sulfamoyl, guanidino, nitro, cyano, lower acylamino, carboxy, alkoxycarbonyl or carbamoyl and p is 0, 1, 2 or 3; or
a group of formula

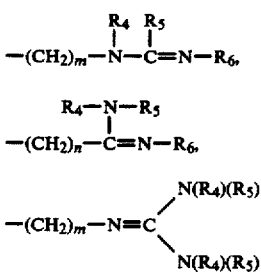

wherein
$R_4$, $R_5$ and $R_6$ may be the same or different and each represents hydrogen or lower alkyl or $R_4$ and $R_6$ and/or $R_5$ and one of the $CH_2$ groups may be joined to form a ring as may $R_5$ and $R_6$ in formula II and $R_4$ and $R_5$ in IIa and IIb, which rings may be unsubstituted or mono- or poly-substituted by alkyl, hydroxy, carboxy or di-(lower)-alkylamino, m is 2 or 3, and
n is 1, 2 or 3
with the proviso that when $R_1$ is hydrogen and the group containing it has R-configuration, $R_2$ is other than acetylaminoethyl; or protected forms and/or physiologically-hydrolysable and acceptable ester forms thereof; in free acid or salt form or in the form of zwitter-ions.

The compounds of the invention may be prepared
(A) by introducing a group $—S—R_2$ into a compound of formula III

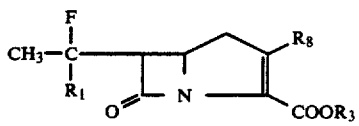

wherein
$R_1$ and $R_2$ are as defined above,
$R_8$ represents a leaving group
$R_3$ represents a protecting group or a physiologically hydrolysable and acceptable ester group or
(B) by exchanging the OH group in a compound of formula IV

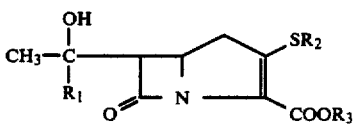

or a precursor thereof for fluoro, whereby in formula IV, $R_1$, $R_2$ and $R_3$ are as defined above, and if required deprotecting a compound thus obtained or if required converting a compound thus obtained into or into another physiologically hydrolysable—and acceptable—ester form and/or protected form thereof and recovering the compound thus obtained in free acid or salt form or in the form of a zwitterion.

Process (A) may be carried out in conventional manner for example in an inert solvent such as an aromatic hydrocarbon e.g. benzene; or acetonitrile and preferably at reduced temperatures e.g. ca 0° C.

Process (B) may be carried out in conventional manner e.g. employing a dialkylaminosulfurtrifluoride such as diethylaminosulfurtrifluoride.

The removal of protecting groups is carried out in conventional manner as is the isolation and purification of the products obtained.

The preparation and interconversion of ester, protected and salt forms is also carried out in conventional manner.

Processes for preparing carbapenems in their various forms are also described in the literature for example in European Patent Application Publications Nos. 1628, 10316, 17992, 37080, 37081, 388869, 50334, 33209, 44142, 60612, 61231, 44170, 59478, 58317 and can where appropriate be employed analogously for preparing compounds according to the invention.

The starting materials of formula III are new and can be prepared by introducing the group $R_8$ into a compound of formula V

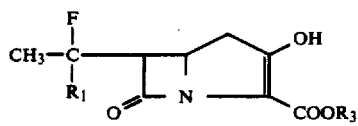  V wherein

R₁, R₃ and R₈ are as defined above.

Examples of leaving groups R₈ are those formed by reaction of the hydroxy group with a phosphoricacid-ester chloride e.g. with phosphoric acid diphenylester chloride or with a sulphonic acid e.g. with p-toluene sulphonic acid.

The compounds of formula IV can be prepared analogously to process (A) above from compounds of formula Va

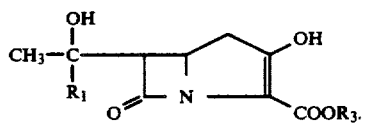  Va

The process is conventional and comprises introduction of the group R₈ followed by group —S—R₂.

The compounds of formula V are also new and can be prepared by example according to the following reaction schemes or analogously to methods described in the above mentioned reaction schemes.

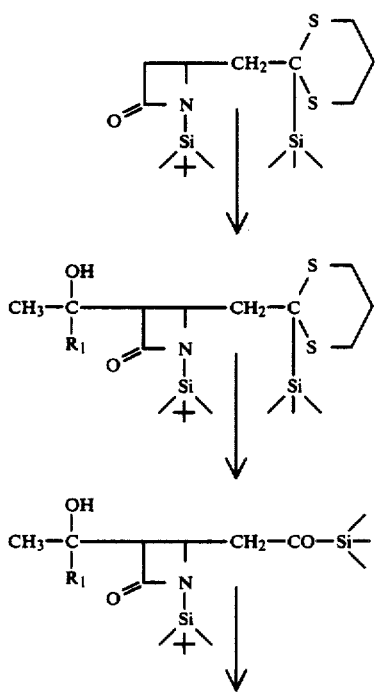

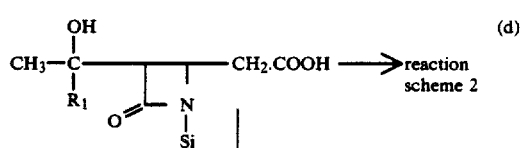 (d)

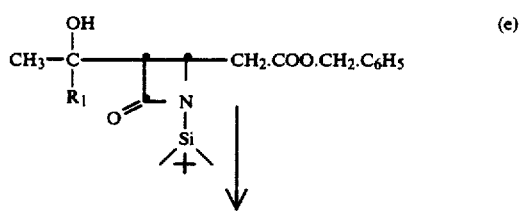 (e)

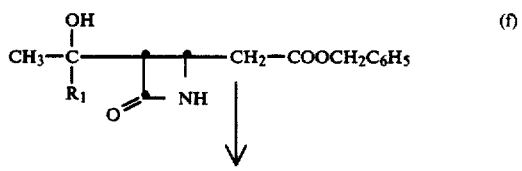 (f)

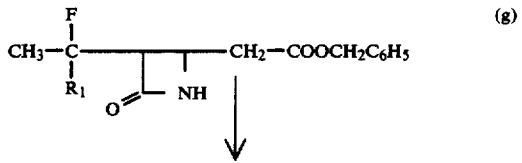 (g)

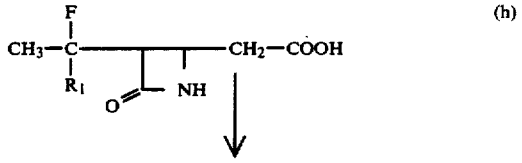 (h)

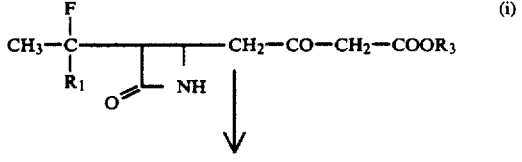 (i)

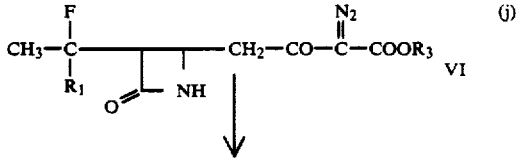 (j)

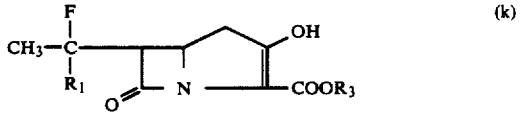 (k)

REACTION SCHEME 2

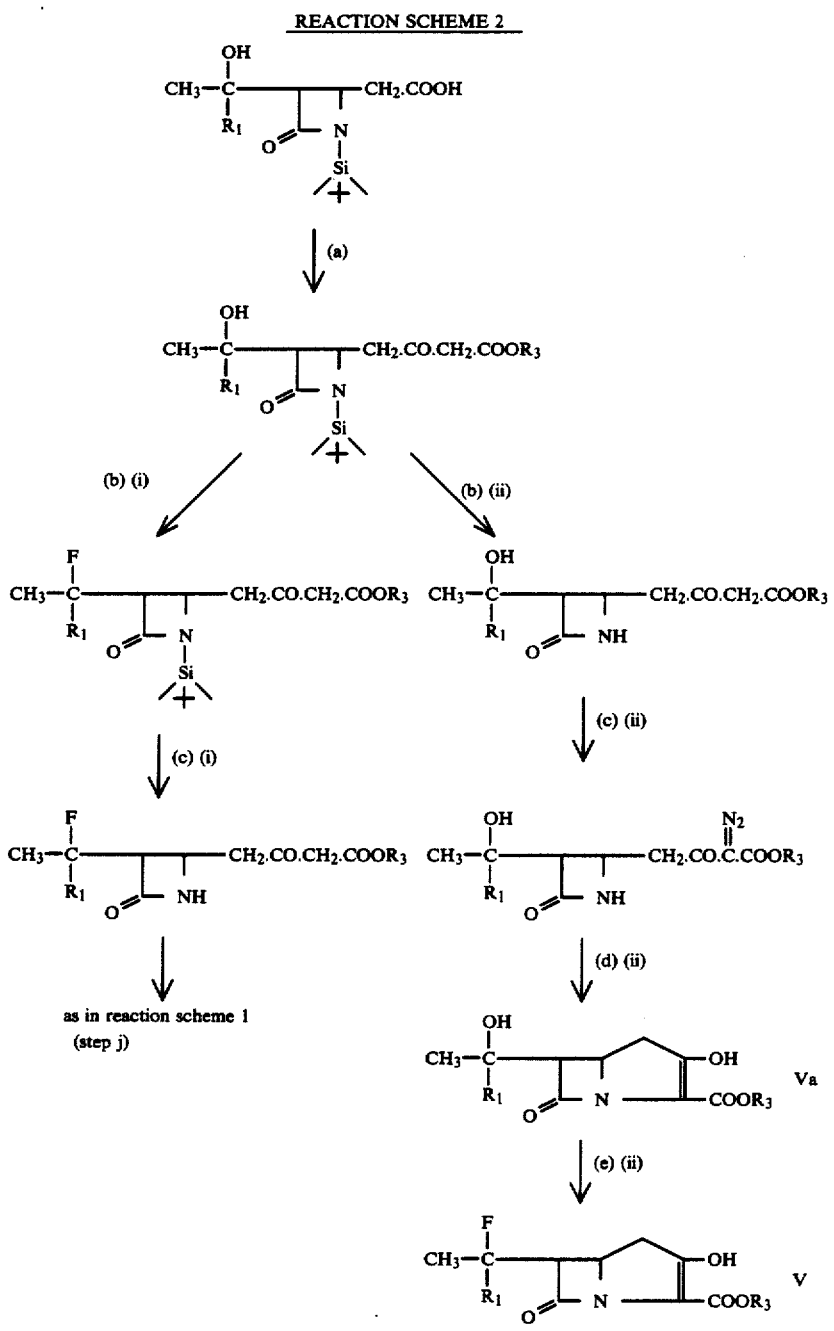

The reactions shown in these schemes can be carried out using procedures conventional for the type of reaction involved. Cyclisation can for example be carried out in an inert solvent such as an aromatic hydrocarbon e.g. benzene in the presence of a transitional metal catalyst. Examples of a transitional metal catalyst are rhodium(II)-acetate or copper acetylacetonate.

The compounds of formula V and Va can exist in the following tautomeric forms

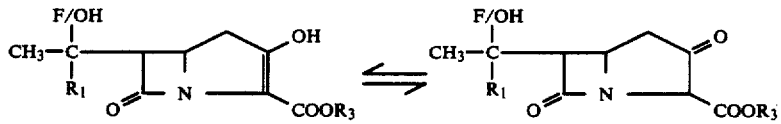

The remaining intermediates are either known or can be prepared analogously to known methods and/or as described hereinafter in the examples.

Carbapenems such as those of the present application contain 2 centres of chirality in the ring (5 and 6)

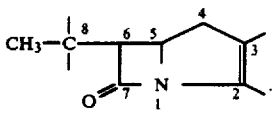

They can be present in the various configurations as 6R,5R-, 6S,5S-, 6S,5R- or 6R,5S-isomers or as mixtures thereof. When the starting materials employed are in a particular configuration the end products obtained will have the same configuration and mixed starting materials will produce mixed end products. The configuration of these compounds thus does not alter during reactions such as (A) or (B) above. Mixtures of isomers can be separated by conventional methods such as fractional crystallisation.

It is known that the biological activity can be attributed to compounds, wherein the 5-position is in R-configuration.

A further centre of chirality is present when $R_1$ is hydrogen and this also remains unaffected during reactions such as (A) above. In reactions such as (B), however, where fluorine is introduced, inversion occurs. The fluorination of an 8-R-hydroxy starting material will yield an 8-S-fluoro end product and vice-versa.

The compounds of formula I in free form or easily cleavable ester form are useful as chemotherapeutic, in particular anti-microbial agents as indicated by their inhibiting effect against various bacteria, e.g. *Pseudomonas aeroginosa, Enterobacter cloacae, Enterbacter agglomerans, Staphylococcus epidermidis, Streptococcus aronson, Streptococcus pneumoniae, Aerococcus viridans, Staphylococcus aureus, Streptococcus pyogenes, Streptococcus faecalis, Escherichia coli, Proteus vulgaris, Proteus mirabilis, Proteus morganii, Klebsiella pneumoniae, Serratia marcescens* and *Salmonella typhimurium* in vitro in series dilution tests at concentrations of, for example, 0.001 to 50 ug/ml, and in vivo in the mouse at dosages of, for example, about 0.1 to 100 mg/kg of animal body weight.

The compounds also possess an inhibiting effect against β-lactamases at concentration between 0.1 and 10 ug/ml. The enzymatic activity of β-lactamase-preparations of gram-positive and gram-negative bacteria may be tested using the chromogenic substrate Nitrocefin (Lit: C. H. O'Callaghan et al., Novel method for detection of β-lactamases by using a chromogenic cephalosporin substrate; Antimicrobial Agent and Chemotherapy, Vol. 1, No. 4, 283–288/1972). The inhibition of β-lactamase is tested in 0.1M phosphatebuffer (pH=7.0) using the same substrate. The enzymes are preincubated together with the inhibitors at appropriate concentrations at 25° C. or the inhibitors and the substrate (Nitrocefin) are added simultaneously and the inhibition of substratehydrolysis caused by the inhibitors in comparison to the noninhibited hydrolysis is measured. The activity is expressed in % inhibition or in $IC_{50}$(=concentration of inhibitor, which inhibits 50% of the enzyme).

This inhibiting effect is also noticeable in the marked synergism demonstrated with other β-lactam antibiotics against β-lactamase producing bacteria. The compounds of the present invention are stable to β-lactamases.

The compounds are therefore useful as chemotherapeutics in particular as antibacterially active antibiotics.

For this use the effective dosage will, of course, vary depending on the particular compound employed, mode of administration and the treatment desired. However, in general, satisfactory results can be obtained when the compounds are administered at a daily dosage of from about 15 to 100 mg/kg of animal body weight, suitably given in divided doses two to four times daily. For most larger mammals, the total daily dose is from about 1 to 6 g and dosage froms suitable for internal administration suitably contain 250 to 3000 mg of a compound in admixture with a solid or liquid pharmaceutical carrier or diluent. The compounds of formula I may be administered in similar manner as known standards for use in such indications e.g. Cefotaxim. The suitable daily dosage for a particular compound will depend on a number of factors such as its relative potency of activity. It has for example been determined that the preferred compounds of this invention namely (5RS,6RS)-1-Aza-6-[1(RS)-fluorethyl]-3-[N,N,N'-trimethylcarbamido)methyl]thio-7-oxobicyclo]3.2.0-]hept-2-ene-2-carboxylic-acid and (5RS,6RS)-1-Aza-6-[1(RS)-fluorethyl]-3-[N,N-dimethylcarbamido)methyl]thio-7-oxobicyclo[3.2.0]hept-2-ene-2-carboxylicacid exhibited a curative dose of ca. 4 mg/kg in the model of Streptococcus septiacaemic infections in mice compared with 5 mg/kg for Cefotaxim. It is therefore indicated that those compounds may be administered at similar or lower dosages than conventionally employed Cefotaxim.

Compounds which contain a free salt forming group can be employed in this form or in the form of a chemotherapeutically acceptable salt thereof, which forms have the same order of activity as the free forms. Suitable salt forms include alkali and alkaline earth metal and ammonium or amino acid salt forms.

Compounds may be admixed with conventional chemotherapeutically acceptable diluents and carriers, and administered in such forms as tablets or capsules or parenterally. Such compositions also form part of the invention.

The invention therefore also concerns a method of combating bacteria comprising administering to a subject in need of such treatment an effective amount of a compound of formula I or a chemotherapeutically acceptable salt thereof and such compounds for use as chemotherapeutic agents, in particular anti-bacterially active antibiotics.

Lower alkyl moieties contain 1 to 6 (e.g. 1–4) esp. 1 or 2 carbon atoms. Correspondingly alkenyl and alkynyl moieties contain 2 to 4 particularly 2 or 3 carbon atoms. Cycloalkyl groups contain preferably 3 to 6 carbon atoms.

By lower acylaminoalkyl is to be understood e.g. —CH$_2$CH$_2$.NH.CO.C$_2$H$_5$, —CH$_3$; —CH$_2$CH$_2$.NH.CO.CH$_2$.C$_6$H$_5$; —CH$_2$CH$_2$.NH.CO.CH$_2$CH$_2$.NH$_2$; —CH$_2$CH$_2$.NH.CO.CH$_2$.NH$_2$. Heterocycles as $R_7$ include e.g.

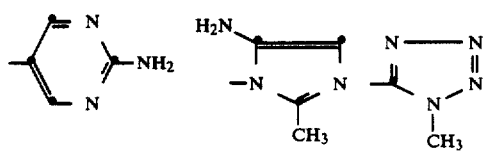

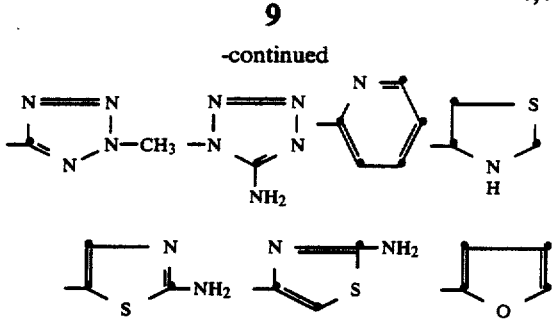

and morpholino.

Protecting groups are those conventionally employed in antibiotics chemistry to protect OH, NH₂ and COOH groups. They include p-nitrobenzyl, p-bitrobenzyloxycarbonyl, t-butyl-dimethylsilyl, trimethylsilyl.

Physiologically hydrolysable- and acceptable-ester groups (also known as easily cleavable ester groups) are those which are hydrolysable under physiological conditions to yield bases which are themselves physiologically acceptable, such esters include acetoxymethyl, 1-acetoxyethyl, 1-ethoxycarbonyloxyethyl, 5-indanyl or preferably, pivaloyloxymethyl, hexanoyloxymethyl, phthalidyl, ethoxycarbonylmethoxymethyl or 3-ethoxycarbonyl-1-acetonyl.

It will be appreciated that certain protecting groups can also be physiologically hydrolysable—and acceptable—groups and vice versa.

Preferred substituents are $R_1=$
(a) H; b) CH₃

$R_2=$
(a) lower alkyl optionally mono- or di-substituted by amino, mono- or di-lower alkylamino, acylamino, carboxy;
(b) —(CH₂)$_p$—R₇
(c) II, IIa or IIb preferably IIa $R_4, R_5, R_6=$
(a) H, Alkyl especially methyl
(b) closed rings $R_7=$
(a) individual heterocycles as listed above
(b) methyltetrazolyl, morpholinyl p=0, 1, 2, 3 or preferably 0 or 2
m=2 or 3 preferably 2
n=1, 2, or 3 preferably 1

Combinations of these meanings and the preferred forms thereof are especially interesting. Examples are $R_1$=hydrogen or methyl; $R_2$=lower alkyl, optionally mono- or disubstituted by amino, alkylamino, dialkylamino, acylamino, carboxy, imino, alkylimino and/or a heterocycle, e.g. methyltetrazolyl or morpholinyl.

Examples of particular compound groups of formula I are those wherein $R_1$ represents hydrogen and $R_2$ represents hydrogen, lower alkyl, lower alkenyl, cycloalkyl which may be substituted by amino, mono- or di-(lower)-alkylamino, lower acylamino, carboxy, lower alkoxy carbonyl or carbamoyl whereby when a cycloalkyl group is substituted by amino or mono- or di-(lower)-alkylamino the nitrogen thereof may form part of the ring; or a group of formula II or IIa, wherein $R_4$, $R_5$ and $R_6$ may be the same or different and represent hydrogen or lower alkyl and m and n are as defined above and the carboxy group at position two is in free form or in protected or easily cleavable ester form or in the form of a salt with an organic or inorganic cation. (Compound Group P1 (2))

A further group is that wherein $R_1$ represents hydrogen or methyl, $R_2$ represents hydrogen, lower alkyl, lower alkenyl, cycloalkyl which may be substituted by amino, mono- or di-(lower)-alkylamino, lower acylamino, carboxy, lower alkoxy carbonyl or carbamoyl whereby when a cycloalkyl group is substituted by amino or mono- or di-(lower)-alkylamino the nitrogen thereof may form part of the ring; a group of formula —(CH₂)$_p$—R₇ wherein p represents 0, 1, 2 or 3 and R₇ represents phenyl or a 5- or 6-membered, saturated or unsaturated heterocycle containing one or more heteroatoms selected from O, S and/or N; or a group of formula II or IIa wherein $R_4$, $R_5$ and $R_6$ may be the same or different and represent hydrogen or lower alkyl and m and n are as defined above and the carboxy group at position two is in free form or in protected or easily cleavable ester form or in the form of a salt with an organic or inorganic cation. (Compound Group P3)

Particularly preferred single compounds are (5RS,6RS)-1-aza-6-(1(RS)-fluorethyl)-3-(N-dimethyl-N'-methylamidinomethyltio)-7-oxobicyclo[3.2.0]hept-2-ene-2-carboxylic acid and (5RS,6RS)-1-aza-6-(1-(RS)-fluorethyl)-3-(N-dimethyl-amidinomethylthio]-7-oxobicyclo[3.2.0]hept-2-ene-2-carboxylic acid.

The following examples illustrate the invention whereby temperatures are expressed in degrees centigrade.

EXAMPLE 1

(5RS,6RS)-1-aza-6-[1(RS)-fluorethyl]-3-(2-(4-nitrobenzyloxycarbonyl)aminoethylthio]-7-oxobicyclo[3.2.0-]hept-2-ene-2-carboxylic acid.4-nitrobenzylester (process a)

To an ice-cold solution of 90 mg of (5RS,6RS)-1-aza-3,7-dioxo-6-[1(RS)-fluorethyl]-bicyclo[3.2.0]heptane-2-carboxylic acid.4-nitrobenzylester in 20 ml abs. acetonitrile are added 0.06 ml of diisopropylamine followed by 0.06 ml of phosphoric acid diphenyl ester chloride. After 15 minutes at 0° a further 0.06 ml of diisopropylamine are added followed by 73 mg of 4-nitrobenzyloxycarbonylcysteamine in 5 ml abs. acetonitrile. Stirring is continued for 1 hour at 0° and the reaction mixture then partitioned between ethyl acetate and saturated aqueous NaCl. After drying over MgSO₄ the organic phase is evaporated to dryness and the residue chromatographed over silica gel (eluant: ethylacetate/diisopropylether=9/1).

NMR (CDCl₃): 1.52 (dd, 3, J=25, 6 Hz); 2.7–3.6 (m, 7); 4.26 (tm, 1, J=7 Hz); 4.98 (dq, 1, J=48, 7 Hz); 5.22 (s, 2); 5.26 (d, 1, J=13.5 Hz); 5.52 (d, 1, J=13.5 Hz); 7.53 (d, 2, J=9 Hz); 7.68 (d, 2, J=9Hz); 8.25 (d, 4, J=9 Hz).

Removal of the protecting groups to prepare (5RS,6RS)-3-(2-aminoethylthio)-1-aza-6-[1(RS)-fluorethyl]-7-oxobicyclo[3.2.0]hept-2-ene-2-carboxylic acid can be carried out as follows:

A suspension of 50 mg of (5RS,6RS)-1-aza-6-[1(RS)-fluorethyl]-3-[2-(4-nitrobenzyloxycarbonyl)aminoethylthio]-7-oxobicyclo[3.2.0]hept-2-ene-2-carboxylic acid.4-nitrobenzylester and 50 mg of 10% Pd/C in 20 ml of tetrahydrofuran and 10 ml water are hydrogenated at room temperature and 3 bar hydrogen pressure for 30 minutes in the presence of 5 ml of 0.5M 3-morpholinopropanesulphonic acid-buffer solution (pH 7). After filtration of the catalyst and washing of the residue with water the combined filtrates are extracted with ethylacetate and the aqueous phase freeze-dried. This lyophilisate is purified by chromatography over XAD 2 (eluant: water). Fractions with UV-extinction at 300 nm are combined and lyophilised to give the title product. UV (ph 7-buffer): λmax=295 nm (ε=8000).

EXAMPLE 2

(5RS,6RS)-3-(2-acetylaminoethylthio)-1-aza-6-(1-fluoro-1-methylethyl)-7-oxobicyclo[3.2.0]hept-2-ene-2-carboxylic acid.4-nitrobenzylester (Process a)

To an ice-cold solution of 150 mg of (5RS,6RS)-1-aza-3,7-dioxo-6-(1-fluoro-1-methylethyl)bicyclo[3.2.0]heptane-2-carboxylic acid.4-nitrobenzyl ester in 10 ml abs. acetonitrile are added 0.11 ml of N-ethyldiisopropylamine followed by 0.13 ml of phosphoric acid diphenylester chloride. After 15 min at 0° a further 0.22 ml of N-ethyldiisopropylamine are added followed by 70 mg of N-acetylcysteamine in 5 ml abs. acetonitrile. Stirring is continued at 0° for 1 hour and the residue then partitioned between ethylacetate and saturated aqueous NaCl. The organic phase is dried over MgSO$_4$ and then evaporated to dryness. The residue is chromatographed over silica gel (ethylacetate/acetone=7/3).

EXAMPLE 3

(5RS,6RS)-3-(2-acetylaminoethylthio)-1-aza-6-(1-fluoro-1-methylethyl)-7-oxobicyclo[3.2.0]hept-2-ene-2-carboxylic acid.4-nitrobenzylester (Process b)

To a −78° cooled solution of 0.12 ml of diethylaminosulphurtrifluoride and 75 mg of potassium fluoride in 5 ml abs. dichloromethane is added a solution of 150 mg of (5RS,6RS)-3-(2-acetylaminoetylthio)-1-aza-6-(1-hydroxy-1-methylethyl)-7-oxobicyclo[3.2.0]hept-2-ene-2-carboxylic acid.4-nitrobenzylester in 5 ml abs. dichloromethane. The mixture is stirred for 15 min. at −78° and then mixed with water. After the addition of further dichloromethane the phases are separated and the organic phase washed with saturated NaCl solution, dried over MgSO$_4$ and evaporated to dryness. Chromatography of the residue on silica gel (ethylacetate/acetone=7/3) yields the title compound m.p. 206°-210°.

Analogously to these examples or as otherwise hereinbefore described, the following compounds of formula I may be prepared.

| | | (Configuration: 6RS, 5RS; when R$_3$ = H: 8RS): | | |
|---|---|---|---|---|
| Ex. | R$_1$ | R$_2$ | R$_3$ | phys. chem. data |
| 4 | −CH$_2$−C$_6$H$_4$−NO$_2$ | −CH$_2$CH$_2$.NH.COO.CH$_2$−C$_6$H$_4$−NO$_2$ | H | |
| 5 | Na | −CH$_2$CH$_2$.NH.CO.CH$_3$ | CH$_3$ | |
| 6 | −CH$_2$−C$_6$H$_4$−NO$_2$ | −CH$_2$CH$_2$−N(morpholino) | H | |
| 7 | Na | −CH$_2$CH$_2$−N(morpholino) | H | |
| 8 | Na | −CH$_2$CH$_2$−N(triazolyl-CH$_3$) | H | |
| 9 | Na | −CH$_2$CH$_2$−N(triazolyl-CH$_3$) | CH$_3$ | λmax = 295 |
| 10 | H | −CH$_2$CH$_2$.N=C(N(CH$_3$)$_2$)$_2$ | H | |
| 11 | H | −CH$_2$CH(NH$_2$)(COONa) (D) | H | λmax = 298 |

-continued (Configuration: 6RS, 5RS; when $R_3$ = H: 8RS):

| Ex. | $R_1$ | $R_2$ | $R_3$ | phys. chem. data |
|---|---|---|---|---|
| 12 | $-CH_2-$(4-nitrophenyl) | $-CH_2-C(=N-CH_3)(N(CH_3)_2)$, $C_4F_9SO_3H$ | H | |
| 13 | H | $-CH_2-C(=N-CH_3)(N(CH_3)_2)$, $C_4F_9SO_3H$ | H | |
| 14 | H | $-CH_2-C(=NH)(N(CH_3)_2)$ | H | |
| 15 | H | $-CH_2CH(CH_3)(NH_2)$ | H | $\lambda max = 294$ |
| 16 | $-CH_2-$(4-nitrophenyl) | $-(CH_2)_4.CH_3$ | H | |
| 17 | $-CH_2-$(4-nitrophenyl) | $-(CH_2)_4.CH_3$ | $CH_3$ | |
| 18 | $-CH_2-$(4-nitrophenyl) | pyrrolidine N—COO.CH$_2$—(4-nitrophenyl), COO.CH$_2$—(4-nitrophenyl) | H | |
| 19 | $-CH_2-$(4-nitrophenyl) | $-CH_2.CH(CH_3)(NHCOO.CH_2-$(4-nitrophenyl)$)$ | H | |
| 20 | $-CH_2-$(4-nitrophenyl) | $-CH_2CH_2-N$(tetrazole)$-CH_3$ | $CH_3$ | |
| 21 | $-CH_2-$(4-nitrophenyl) | $-CH_2CH_2-N$(tetrazole)$-CH_3$ | H | |
| 32 | $-CH_2-$(4-nitrophenyl) | $-CH_2.C(=N^{\oplus}H_2)(N(CH_3)_2)$ $Cl^{\ominus}$ | H | |

EXAMPLE 23

(5R,6R)-3-(2-acetylaminoethylthio)-1-aza-6-[1(S)-fluorethyl]-7-oxobicyclo[3.2.0]hept-2-ene-2-carboxylic acid.4-nitrobenzylester Analogously to Example 1.

EXAMPLE 24

(5R,6R)-3-(2-acetylaminoethylthio)-1-aza-[1(S)-fluorethyl]-7-oxobicyclo[3.2.0]hept-2-ene-carboxylic acid.Na-salt Analogously to Example 1. $\lambda max = 298$.

EXAMPLE 25

(+)-(5R,6R)-1-aza-6-[1(R)-fluorethyl]-3-(2S)-[2-(4-nitrobenzyloxycarbonyl)-2-(4-nitrobenzyloxycarbonylamino)-ethylthio]-7-oxobicyclo[3.2.0]hept-3-ene-2-carboxylic acid.4-nitrobenzylester:

0.506 ml of diisopropylethylamine and 0.486 ml of diphenylphosphoric acid ester chloride are added at −30° and with stirring to a solution of 680.4 mg of (5RS,6RS)-3,7-dioxo-6-(1(RS)-fluoroethyl)-1-azabicyclo[3.2.0]heptane-2-carboxylic acid.4-nitrobenzylester in 20 ml of dimethylformamide. The reaction mixture is left standing for 30 minutes at −30° and then mixed with 0.404 ml of diisopropylamine. A solution of 1.016 g of N-(4-nitrobenzyloxycarbonyl)-D-cysteine.4-nitrobenzylester in 4 ml of abs. dimethylformamide is then added dropwise, the mixture stirred for 30 minutes at −30° and then diluted with 200 ml of dichloromethane. The organic solution is washed successively with 140 ml each of 0.1M phosphate buffer of pH 8.4, 6.9 and 8.4 and dried with $Na_2SO_4$. This solution can be used for preparation of the optical isomers.

[The racemate can be obtained by filtering the dichloromethane solution concentrating under vacuum to ca. 20 ml and chromatographing the residue on silica gel (benzene/ethylacetate=3/1). The fractions with UV Rf of 0.30 (benzene/ethylacetate=2/1) are collected and dried.]

For preparation of the isomer the dichloromethane solution is evaporated to dryness, the residue washed with 20 ml of chloroform and dried. The filtrate is evaporated to a sirup and then chromatographed over silica gel (eluant: benzene/ethylacetate=3/1). The fractions are combined and evaporated under reduced pressure to dryness. The residue is treated with 5 ml of chloroform, filtered and washed with 10 ml of chloroform. A weakly yellow, amorphous powder is obtained $[\alpha]_D^{23} = +27.9°$ (c=0.5 in dichloromethane). For further purification this powder is dissolved in 20 ml of dichloromethane and filtered. The filtrate is concentrated to ca. 1 ml and then treated with 1-2 ml of chloroform to give a weakly yellow, amorphous powder $[\alpha]_D^{23} = +29°$ (c=0.5 in dichloromethane).

| Example: | NMR-SPECTRA<br>Spectrum: |
|---|---|
| 2,3<br>(CDCl₃) | 1.49 (d, 3, J = 20 Hz); 1.57 (d, 3, J = 20 Hz); 2.00 (s, 3); 2.87-3.53 (m, 7); 4.32 (td, 1, J = 10 Hz, 2.7); 5.25 (d, 1, J = 13.7 Hz); 5.52 (d, 1, J = 13.7 Hz); 5.89 (br, 1); 7.67 (d, 2, J = 8 Hz); 8.24 (d, 2, J = 8 Hz). |
| 4<br>(CDCl₃) | 1.52 (dd, 3, J = 25 and 6 Hz); 2.7-3.6 (m, 7); 4.26 (tm, 1, J = 7 Hz); 4.98 (dq, 1, J = 48 and 7 Hz); 5.22 (s, 2); 5.26 (d, 1, J = 13.5 Hz); 5.52 (d, 1, J = 13.5 Hz); 7.53 (d, 2, J = 9 Hz); 7.68 (d, 2, J = 9 Hz); 8.25 (d, 4, J = 9 Hz). |
| 5<br>(D₂O) | 1.68 (d, 3, J = 22.5 Hz); 1.74 (d, 3, J = 22.5 Hz); 2.00 (s, 3); 2.85-3.14 (m, 2); 3.16 (dd, 1, J = 17.5 and 9 Hz); 3.28 (dd, 1, J = 17.5 and 9.5 Hz); 3.42 (t, 2, J = 6.5 Hz); 3.65 (dd, 1, J = 17.5 and 9.5 Hz); 3.42 (t, 2, J = 6.5 Hz); 3.65 (dd, 1, J = 26.5 and 2.5 Hz); 4.27 (td, 1, J = 9.5 and 2.5 Hz). |
| 6<br>(CDCl₃/DMSO-d₆) | 1.42 (dd, 3, J = 24 and 7 Hz); 2.45 (t, 4, J = 4.5 Hz); 2.60 (t, 2, J = 7.5 Hz); 2.94-3.10 (m, 2); 3.30-3.45 (m, 2); 3.60 (t, 4, J = 4.5 Hz); 3.66 (ddd, 1, J = 25, 6 and 2.5 Hz); 4.23 (td, 1, J = 9 and 2.5 Hz); 5.03 (dq, 1, J = 49 and 6 Hz); 5.27 (d, 1, J = 14 Hz); 5.45 (d, 1, J = 14 Hz); 6.98 (br, 1); 7.72 (d, 2, J = 9.5 Hz); 8.20 (d, 2, J = 9.5 Hz). |
| 7<br>(D₂O) | 1.58 (dd, 3, J = 25 and 6.5 Hz); 3.06-3.76 (m, 11); 4.02-4.12 (m, 4); 4.48 (td, 1, J = 9 and 3 Hz); 5.28 (dm, 1, J = 52 Hz). |
| 8<br>(D₂O) | 1.43 (dd, 3, J = 26 and 6.5 Hz); 2.59 (s, 3); 2.93 (dd, 1, J = 18 and 9 Hz); 3.02 (dd, 1, J = 18 and 9.5 Hz); 3.56 (ddd, 1, J = 27, 5 and 2.8 Hz); 4.09 (td, 1, J = 9.5 and 2.8 Hz); 5.12 (dm, 1, J = 48 Hz). |
| 10<br>(D₂O) | 1.45 (dd, 3, J = 25 and 6.5 Hz); 2.90-3.03 (m, 12); 3.07-3.57 (m, 6); 3.67 (ddd, 1, J = 28, 5 and 2.5 Hz); 4.29 (td, 1, J = 9 and 2.5 Hz); 5.14 (dm, 1, J = 49 Hz). |
| 11<br>(D₂O) | 1.41 (dd, 3, J = 6 and 25 Hz); 2.80-3.65 (m, 5); 3.75-3.97 (m, 1); 4.29 (dt, 1, J = 2.5 and 8.5 Hz); 5.11 (m, 1, J = 6, 7.5 and 48.8 Hz); |
| 12<br>(CDCl₃/DMSO-d₆) | 1.46 (dd, 3, J = 24 and 7 Hz); 3.10-3.57 (m, 11); 3.63 (ddd, 1, J = 24, 6 and 2.5 Hz); 4.15 (d, 1, J = 12.5 Hz); 4.27 (d, 1, J = 12.5 Hz); 4.33 (td, 1, J = 9 and 2.5 Hz); 5.05 (dm, 1, J = 49 Hz); 5.29 (d, 1, J = 14 Hz); 5.51 (d, 1, J = 14 Hz); 7.70 (d, 2, J = 9 Hz); 8.28 (d, 2, J = 9 Hz); 8.90 (br, 1). |
| 13<br>(D₂O) | 1.46 (dd, 3, J = 25 and 6.5 Hz); 3.12 (s, 3); 3.15 (s, 3); 3.25 (dd, 1, J = 18 and 9 Hz); 3.32 (dd, 1, J = 18 and 10 Hz); 3.36 (s, 3); 3.71 (ddd, 1, J = 27, 5 and 2.8 Hz); 4.01 (d, 1, J = 12.5 Hz); 4.09 (d, 1, J = 12.5 Hz); 4.35 (td, 1, J = 9.5 and 2.8 Hz); 5.25 (dm, 1, J = 49 Hz). |
| 14<br>(D₂O) | 1.44 (dd, 3, J = 25 and 6.5 Hz); 3.14 (d, 2, J = 9.5 Hz); 3.17 (s, 3); 3.30 (s, 3); 3.71 (ddd, 1, J = 28, 5 and 2.5 Hz); 4.00 (s, 2); 4.31 (td, 1, J = 9.5 and 2.5 Hz); 5.15 (dm, 1, J = 49 Hz). |
| 16<br>(CDCl₃) | 0.70-1.05 (m, 3); 1.22-1.60 (m, 6); 1.52 (dd, 3, J = 25 and 7 Hz); 2.67-3.00 (m, 2); 3.02-3.54 (m, 3); 4.28 (dt, 1, J = 9.5 and 2.5 Hz); 5.02 (dm, 1, J = 49 Hz); 5.26 (d, 1, J = 12.5 Hz); 5.52 (d, 1, J = 12.5 Hz); 7.68 (d, 2, J = 9 Hz); 8.26 (d, 2, J = 9 Hz). |
| 17<br>(CDCl₃) | 0.8-1.02 (m, 3); 1.20-1.56 (m, 6); 1.51 (d, 3, J = 21.5 Hz); 1.58 (d, 3, J = 21.5 Hz); 2.86 (t, 2, J = 7 Hz); 3.11 (dd, 1, J = 16 and 7 Hz); 3.33 (dd, 1, J = 16 and 8 Hz); 3.39 (dd, 1, J = 18 and 3 Hz); 4.32 (dt, 1, J = 8 and 3 Hz); 5.27 (d, 1, J = 14 Hz); 5.55 (d, 1, J = 14 Hz); 7.70 (d, 2, J = 9 Hz); 8.26 (d, 2, J = 9 Hz). |
| 18<br>(CDCl₃) | 1.51 (dd, 3, J = 24.5 and 7 Hz); 2.0-2.4 (m, 2); 2.64-3.04 (m, 1); 3.10-3.90 (m, 5); 4.0-4.9 (m, 2.5); 5.1-5.64 (m, 6.5); 7.34-7.67 (m, 6); 8.04-8.36 (m, 6). |
| 19<br>(CDCl₃) | 1.20-1.37 (m, 3); 1.50 (dd, 3, J = 24 and 8 Hz); 2.62-3.56 (m, 6); 3.95-4.30 (m, 1); 4.80-5.32 (m, 1); 5.22 (s, 2); 5.28 (d, 1, J = 14.5 Hz); 5.54 (d, 1, J = 14.5 Hz); 7.52 (d, 2, J = 9 Hz); 7.70 (d, 2, J = 9 Hz); 8.26 (d, 4, J = 9 Hz). |
| 20<br>(CDCl₃) | 1.48 (d, 3, J = 21.5 Hz); 1.56 (d, 3, J = 21.5 Hz); 2.56 (s, 3); 2.70-3.53 (m, 5); 4.25 (td, 1, J = 9.5 and 2.5 Hz); 4.51 (t, 2, J = 7 Hz); 5.28 (d, 1, J = 13.5 Hz); 5.52 (d, 1, J = 13.5 Hz); 7.68 (d, 2, J = 9 Hz); 8.28 (d, 2, J = 9 Hz). |
| 21<br>(CDCl₃) | 1.50 (dd, 3, J = 24.5 and 6.5 Hz); 2.56 (s, 3); 2.74-3.56 (m, 5); 4.24 (td, 1, J = 9 and 2.5 Hz); 4.30-4.60 (m, 2); 5.02 (dm, 1, J = 49 Hz); 5.27 (d, 1, J = 14.5 Hz); 5.49 (d, 1 J = 14.5 Hz); 7.67 (d, 2, J = 9 Hz); 8.27 (d, 2, J = 9 Hz). |
| 22<br>(CDCl₃/DMSO-d₆) | 1.45 (dd, 3, J = 24 and 6.5 Hz); 3.11 (s, 3); 3.23 (s, 3); 3.30-3.60 (m, 2); 3.71 (ddd, 1, J = 25, 5.5 and 2.5 Hz); 4.26 (s, 2); 4.30 (td, 1, J = 10 and 2.5 Hz); 5.04 (dm, 1, J = 48 Hz); 5.30 (d, 1, J = 15 Hz); 5.50 (d, 1, J = 15 Hz); 7.72 (d, 2, J = 9 Hz); 8.25 |

NMR-SPECTRA -continued

| Example: | Spectrum: |
|---|---|
| 23 (CDCl₃/ Aceton-d₆) | (d, 2, J = 9 Hz); 9.03 (br, 1); 9.75 (br, 1). 1.57 (dd, 3, J = 23.5 and 6.3 Hz); 2.0 (s, 3); 2.87–3.74 (m, 7); 4.34 (td, 1, J = 9 and 2.7 Hz); 5.02 (dm, 1, J = 49 Hz); 5.30 (d, 1, J = 16 Hz); 5.55 (d, 1, J = 16 Hz); 6.78 (br, 1); 7.72 (d, 2, J = 9 Hz); 8.28 (d, 2, J = 9 Hz). |

The required starting materials can be prepared as follows:

(A)

(5RS,6RS)-1-aza-3,7-dioxo-6-[1(RS)-fluorethyl]-bicyclo[3.2.0]heptane-2-carboxylic acid.4-nitrobenzylester (for examples 4, 6–8, 10–16, 18, 19, 21): [reaction scheme 1 steps g) to k)]

(a)

(3RS,4RS)-3-[1(RS)-fluoroethyl]-2-oxoazetidine-4-yl-acetic acid benzylester

To a −78° cooled solution of 1.5 ml of diethylaminosulphurtrifluoride in 4 ml abs. dichloromethane is added a solution of 2.52 g of (3SR,4RS)-3-[1(SR)-hydroxyethyl]-2-oxoazetidine-4-yl-acetic acid benzyl ester (prepared analogously to D. G. Melillo et. al., Tetrahedron Letters 21, 2783 [1980]) in 4 ml abs. dichloromethane. The mixture is stirred for 5 minutes at −78° and mixed with excess cold saturated NaHCO₃. After addition of further dichloromethane the phases are separated, the organic phase dried over magnesium sulphate and evaporated to dryness. Chromatography of the residue over silica gel (cyclohexane/ethylacetate=2/1) yields the title compound m.p. 40°–43°.

IR (CHCl₃): 1765, 1730 cm⁻¹.

NMR (CDCl₃): 1.45 (dd, 3, J=24, 6.5 Hz); 2.68 (dd, 1, J=16, 9 Hz); 2.86 (dd, 1, J=16, 5.5 Hz); 3.01 (ddd, 1, J=18.5, 7, 2.5 Hz); 4.02 (ddd, 1, J=9, 5.5, 2.5 Hz); 4.97 (dq, 1, J=48, 6.5 Hz); 5.18 (s, 2); 6.25 (br, 1); 7.40 (s, 5).

(b)

(3RS,4RS)-3-[1(RS)-fluorethyl]-2-oxoazetidine-4-yl-acetic acid

A mixture of 700 mg of the corresponding benzylester and 50 mg of 10% Pd/C in 50 ml of ethanol is hydrogenated at a hydrogen pressure of 10 bars for 30 mins. Filtration and concentration of the filtrate to dryness yields the title compound m.p. 137°–141°.

IR (KBr): 3317, 2983, 2923, 2577, 1720 cm⁻¹.

NMR (CDCl₃/CO₃OD): 1.45 (dd, 3, J=23.5, 6.5 Hz); 2.62 (dd, 1, J=16, 9 Hz); 2.80 (dd, 1, J=16, 4.5 Hz); 3.01 (ddd, 1, J=21, 6.5, 2.5 Hz); 4.00 (ddd, 1, J=9, 4.5, 2.5 Hz); 4.98 (dq, 1, J=49.5, 6.5 Hz).

(c)

[(3RS,4RS)-3-[1(RS)-fluorethyl]-2-oxoazetidine-4-yl]-(2-oxo)butyric-acid.4-nitrobenzylester A solution of 352 mg of (3RS,4RS)-3-[1(RS)-fluorethyl]-2-oxo-azetidine-4-yl-acetic acid in 15 ml abs. tetrahydrofuran is stirred for 5 hours at room temperature with 359 mg of carbonyldiimidazole. At the same time a solution of 995 mg of malonic acid mono-4-nitrobenzylester in 15 ml abs. tetrahydrofuran is mixed with 253 mg of magnesium ethanolate and stirred for 1 hour at room temperature. The two solutions are combined and stirred for 16 hours at room temperature. The mixture is diluted with ether and washed with 0.1N HCl. The aqueous phase is extracted once more with ethylacetate and the combined extracts dried over MgSO₄ and evaporated to dryness. Chromatography of the residue of silica gel (ethylacetate) yields the title compound m.p. 115°–118°.

IR (CH₂Cl₂): 3407, 2928, 1770, 1720, 1525, 1350 cm⁻¹.

NMR (CDCl₃): 1.47 (dd, 3, J=18, 7 Hz); 2.86 (dd, 1, J=18.5, 10 Hz); 2.94 (ddd, 1, J=18, 7, 2 Hz); 3.09 (dd, 1, J=18.5, 4 Hz); 3.58 (s, 2); 4.00 (ddd, 1, J=10, 4, 2 Hz); 4.93 (dq, 1, J=48, 7 Hz); 5.28 (s, 2); 6.18 (br, 1); 7.52 (d, 2, J=9 Hz); 8.26 (d, 2, J=9 Hz).

(d)

[(3RS,4RS)-3-[1(RS)-fluorethyl]-2-oxoazetidine-4-yl]-(2-oxo-3-diazo)butyric-acid.4-nitrobenzylester To an ice-cooled solution of 469 mg of (3RS,4RS)-3-[1-(RS)-fluorethyl]-2-oxoazetidine-4-yl-(2-oxo)butyric-acid.4-nitrobenzylester and 374 mg of 4-carboxybenzenesulfonylazide in 15 ml of ethylacetate are added in one lot 0.67 ml of triethylamine. After removal of the cooling bath stirring is continued at room temperature during which time a precipitate forms. This is filtered off and the filtrate washed once with saturated NaHCO₃ and dried over MgSO₄. Removal of the solvent yields the title compound m.p. 138°–141°.

IR (KBr): 3414, 3204, 2135, 1760, 1720, 1650, 1520 cm⁻¹.

NMR (CDCl₃): 1.45 (dd, 3, J=23.5, 7 Hz); 3.04 (ddd, 1, J=19, 7, 2 Hz); 3.06 (dd, 1, J=18, 10 Hz); 3.44 (dd, 1, J=18, 4 Hz); 4.04 (ddd, 1, J=10, 4, 2 Hz); 4.98 (dq, 1, J=48, 7 Hz); 5.38 (s, 2); 6.17 (br, 1); 7.58 (d, 2, J=9 Hz); 8.31 (d, 2, J=9 Hz).

(e)

(5RS,6RS)-1-aza-3,7-dioxo-6-[1(RS)-fluorethyl]-bicyclo[3.2.0]heptane-2-carboxylic acid.4-nitrobenzylester A suspension of (3RS,4RS)-3-[(1(RS)-fluorethyl]-2-oxoazetidine-4-yl-(2-oxo-3-diazo)butyric-acid.4-nitrobenzylester and 2 mg of rhodium(II)-acetate in 5 ml abs. benzene is warmed for 5 mins under argon. After cooling to room temperature the catalyst is filtered off and the filtrate evaporated to dryness. The title compound is obtained as a colourless form resin.

IR (CH₂Cl₂): 1775, 1750, 1525, 1350 cm⁻¹.

NMR (CDCl₃): 1.52 (dd, 3, J=25, 7 Hz); 2.52 (dd, 1, J=18.5, 7.5 Hz); 2.96 (dd, 1, J=18.5, 7 Hz); 3.35 (ddd, 1, J=18, 8, 2 Hz); 4.20 (td, 1, J=7, 2 Hz); 4.80 (s, 1); 5.11 (dm, 1, J=48 Hz); 5.26 (d, 1, J=12.5 Hz); 5.37 (d, 1, J=12.5 Hz); 7.58 (d, 2, J=9 Hz); 8.29 (d, 2, J=9 Hz).

(B)

(5RS,6RS)-1-aza-3,7-dioxo-6-(1-fluoro-1-methylethyl(-bicyclo[3.2.0]heptane-2-carboxylic acid.4-nitrobenzylether (for examples 2, 5, 9, 17 and 20): [(reaction scheme 1(a) to (k)]

(a)

2-oxo-3-trans-(1-hydroxy-1-methylethyl)-4-(2-trimethylsilyldithian-2-yl)methyl-1-tert.butyldimethylsilylazetidine To a solution of 10.1 g of diisopropylamine in 500 ml of abs. tetrahydrofuran are added at −75°, 75 ml of 1.6N solution of n-butyllithium in hexane. After 20 mins. at −75°, 20 g of 1-tert.butyldimethyl-2-oxo-4-(2-trimethylsilyldithiane-2-yl)methylazetidine are added followed after 20 mins. by 17 ml abs. acetone. The reaction mixture is diluted with 500 ml saturated NH4Cl and extracted with ethylacetate. Drying and concentration of the extracts yields the title product.

NMR (CDCl3): 0.26 (s, 15); 0.98 (s, 9); 1.24 (s, 3); 1.40 (s, 3); 1.80–2.10 (m, 2); 2.34 (d, 1, J=1Hz); 2.40 (s, 1); 2.60–3.00 (m, 4); 3.19 (d, 1, J=2 Hz); 3.80 (s, 1); 3.90 (m, 1).

(b)

trimethylsilyl-(2-oxo-3-trans-(1-hydroxy-1-methylethyl)-1-tert.butyldimethylsilylazetidine-4-yl)methylketone 28 g of 2-oxo-3-trans-(1-hydroxy-1-methylethyl)-4-(2-trimethylsilyldithian-2-yl)-methyl-1-tert.butydimethylsilylazetidine, 23.65 g red mercuric oxide and 43 g of mercuric chloride are refluxed for 1 hour in 400 ml of 95% methanol. After filtration from the mercury salts the filtrate is concentrated and the residue partitioned between ethylacetate and saturated NH4Cl. Drying and concentration of the organic phase yields the title compound as a colourless oil.

NMR (CDCl3): 0.22 (s, 6); 0.24 (s, 9); 0.98 (s, 9); 1.30 (s, 3); 2.84 (d, 1, j=2 Hz); 2.88 (dd, 1, J=19 and 10 Hz); 3.28 (dd, 1, J=19 and 3.6 Hz); 3.86 (ddd, 1, J=10, 3.6 and 2 Hz).

(c)

1-tert-butyldimethylsilyl-2-oxo-3-trans-(1-hydroxy-1-methylethyl)azetidine-4-yl-acetic acid 5 g of trimethylsilyl-(2-oxo-3-trans-(1-hydroxy-1-methylethyl)-1-tert.butyldimethylsilylazetidine-4-yl)methylketone are refluxed for 1 hour in 120 ml of methanol with 10 ml of 30% hydrogen peroxide. After concentration to dryness the residue is taken up in ethylacetate, extracted twice with 5% aqueous NaHCO3 and the aqueous phase further extracted once with ethylacetate. The aqueous phase is covered with ethylacetate, the pH adjusted to 3.5 with half-concentrated HCl and after separation of the ethylacetate phase again extracted twice with ethylacetate. After drying and removal of the solvent from the combined ethylacetate extracts, the title compound is obtained as a colourless oil.

NMR (CDCl3): 0.22 (s, 3); 0.24 (s, 3); 0.96 (s, 9); 1.32 (s, 3); 1.34 (s, 3); 2.56 (dd, 1, J=19 and 10 Hz); 2.92 (dd, 1, J=19 and 3.6 Hz); 3.11 (d, 1, J=2 Hz); 3.86 (ddd, 1, J=10, 3.6 and 2 Hz).

(d)

1-tert.butyldimethylsilyl-2-oxo-3-(trans)-(1-hydroxy-1-methylethyl)azetidine-4-yl-acetic acid benzylester 5 g 1-tert.butyldimethylsilyl-2-oxo-3-trans-(1-hydroxy-1-methylethyl)azetidine-4-yl-acetic acid, 1.71 ml of benzyl alcohol and 300 mg of 4-dimethylaminopyridine in 30 ml abs. dichloromethane are rapidly mixed with a solution of 4 g of dicyclohexylcarbodiimide and stirred for a further 2 hours at room temperature. After addition of 50 ml of ether and 50 ml of diisopropylether filtration is carried out, the residue carefully washed with ether and the filtrate evaporated to dryness. This residue is chromatographed on a small amount of silica gel to obtain the title compound as a colourless oil.

NMR (CDCl3): 0.16 (s, 3); 0.18 (s, 3); 0.90 (s, 9); 1.24 (s, 3); 1.26 (s, 3); 2.53 (dd, 1, J×16.2 and 10.6 Hz); 2.63 (s, 1); 2.82 (dd, 1, J=16.2 and 4 Hz); 3.02 (d, 1, J=2.7 Hz); 3.83 (dd, 1, J=10.6, 4 and 2.7 Hz); 5.10 (s, 2); 7.37 (s, 5).

(e)

(3SR,4RS)-3-(1-hydroxy-1-methylethyl)-2-oxoazetidine-4-yl-acetic acid benzylester To an ice-cold solution of 3.7 g 1-tert.butyldimethylsilyl-2-oxo-3-(trans)-(1-hydroxy-1-methylethyl)azetidine-4-yl-acetic acid benzylester in 130 ml of methanol/water (9/1) are added 6.6 ml of conc. HCl. This mixture is stirred for 30 minutes at 0° and 3½ hours at 25°. The solution is concentrated and the residue taken up in ethylacetate, washed once with aq. NaCl, dried over MgSO4 and evaporated to dryness to yield the title compound NMR (CDCl3): 1.24 (s. 3); 1.34 (s, 3); 2.60–2.84 (m, 3); 2.87 (d, 1, J=1.8 Hz); 3.94 (ddd, 1, J=8, 6.3 and 1.8 Hz); 5.13 (s, 2); 6.57 (br, 1); 7.37 (s, 5).

(f)

(3RS,4RS)-3-(1-fluoro-1-methylethyl)-2-oxoazetidine-4-yl-acetic acid benzylester To a −78° cold solution of 3 ml of diethylaminosulphurtrifluoride and 1.7 g of potassium fluoride in 80 ml of dichloromethane is added a solution of 3.2 g of (3SR,4RS)-3-(1-hydroxy-1-methyethyl)-2-oxoazetidine-4-yl acetic acid benzylester in 170 ml of dichloromethane. This mixture is stirred for 15 minutes at −78° and then mixed with water. After addition of further dichloromethane the phases are separated and the organic phase washed with saturated NaCl, dried over MgSO4 and evaporated to dryness. Chromatography of the residue over silica gel (ethylacetate/cyclohexane=1/1) yields the title compound m.p. 112°–116°.

NMR (CDCl3): 1.42 (d, 3, J=21.5 Hz); 1.52 (d, 3, J=21.5 Hz); 2.62 (dd, 1, J=16.2 and 9 Hz); 2.84 (dd, 1, J=16.2 and 4.5 Hz); 3.00 (dd, 1, J=21.5 and 2.7 Hz); 4.01 (ddd, 1, J=9, 4.5 and 2.7 Hz); 5.16 (s, 2); 6.14 (br, 1); 7.39 (s, 5).

(g)

(3RS,4RS)-3-(1-fluoro-1-methylethyl)-2-oxoazetidine-4-yl-acetic acid

A mixture of 1 g of (3RS,4RS)-3-(1-fluoro-1-methylethyl)-2-oxoazetidine-4-yl acetic acid benzylether and 0.5 g of 10% Pd/C in 80 ml of methanol is hydrogenated for 3½ hours a hydrogen pressure of 1 bar. Filtration and concentration of the filtrate to dryness yields the title compound m.p. 118°–122°.

NMR (CDCl3/DMSO-d6): 1.43 (d, 3, J=21.6 Hz); 1.52 (d, 3, J=21.6 Hz); 2.57 (dd, 1, J=16.2 and 9 Hz); 2.72 (dd, 1, J=16.2 and 5.4 Hz); 3.00 (dd, 1, J=23.5 and 2.5 Hz); 3.96 (ddd, 1, J=9, 5.4 and 2.5 Hz).

(h)

[(3RS,4RS)-3-(1-fluoro-1-methylethyl)-2-oxazetidine-4-yl]-(2-oxo)butyric-acid.4-nitrobenzylester 700 mg of (3RS,4RS)-3-(1-fluoro-1-methylethyl)-2-oxoazetidine-4-yl-acetic acid are dissolved in 20 ml of tetrahydrofuran, mixed at −20° with 600 mg of carbonyldiimidazole and stirred for 3 hours at +20°. At the same time 900 mg of malonic acid 4-nitrobenzylester and 420 mg of magnesium ethanolate are suspended in 20 ml of tetrahydrofuran and stirred for 3 hours at room temperature. The first obtained solution is now added to this second solution and stirred overnight. The mixture is then poured onto ether and extracted with 1N HCl and water. Drying of the organic phase followed by column chromatography of the residue yields the title compound.

NMR (CDCl$_3$): 1.44 (d, 3, J=21.5 Hz); 1.52 (d, 3, J=2.15 Hz); 2.86 (dd, 1, J=18 and 10 Hz); 2.98 (dd, 1, J=20 and 3.5 Hz); 3.06 (dd, 1, J=18 and 4.5 Hz); 3.58 (s, 2); 4.02 (dt, 1, J=10 and 3.5 Hz); 5.30 (s, 2); 6.16 (br, 1); 7.58 (d, 2, J=9 Hz); 8.28 (d, 2, J=9 Hz).

(i)

(3RS,4RS)-3-(1-fluoro-1-methylethyl)-2-oxoazetidine-4-yl-(2-oxo-3-diazo)butyric-acid.4-nitrobenzylester To an ice-cold solution of 0.22 g (3RS,4RS)-3-(1-fluoro-1-methylethyl)-2-oxoazetidine-4-yl-(2-oxo)-butyric-acid.4-nitrobenzylester and 0.17 g of 4-carboxybenzenesulphonylazide in 20 ml of acetonitrile are added 0.34 ml of triethylamine. After removal of the cooling bath stirred is continued for 30 mins. at room temperature. The mixture is mixed with 100 ml of ethylacetate, washed with 5% NaHCO$_3$ and then water and dried over MgSO$_4$. Removal of the solvent yields the title compound.

(j)

(5RS,6RS)-1-aza-3,7-dioxo-6-(1-fluoro-1-methylethyl)-bicyclo[3.2.0]heptane-2-carboxylic acid.4-nitrobenzylester A suspension of 0.19 g of (3RS,4RS)-3-(1-fluoro-1-methylethyl)-2-oxoazetidine-4-yl-(2-oxo-3-diazo)butyric-acid.4-nitrobenzylester and 20 mg rhodium(II)-acetate in 100 ml of benzene are heated for 10 minutes at 80° under argon. After cooling to room temperature the catalyst is filtered off and the filtrate evaporated to dryness to obtain the title compound.

(C)

(5RS,6RS)-1-aza-3,7-dioxo-6-(1-fluoro-1-methylethyl)-bicyclo[3.2.0]heptane-2-carboxylic acid.4-nitrobenzylester (for examples 2, 5, 9, 17 and 20):
[(reaction scheme 2(a), (b)(ii) to (e)(ii)]

(a)

1-tert.butyldimethylsilyl-2-oxo-3-(trans)-[(1-hydroxy-1-methylethyl)azetidine-4-yl]-(2-oxo)butyric-acid.4-nitrobenzylether 1.2 g of 1-tert.butyldimethylsilyl-2-oxo-3-trans-(1-hydroxy-1-methylethyl)azetidine-4-yl-acetic acid are dissolved in 20 ml of tetrahydrofuran, mixed at −20° with 1 g of carbonyldiimidazole and stirred for 3 hours at 20°. At the same time 1.9 g of malonic acid -4-nitrobenzylester and 0.7 g of magnesium ethanolate are suspended in 30 ml of tetrahydrofuran and stirred for 3 hours at room temperature. Further reaction and extraction takes place analogously to (B)(h).

NMR (CDCl$_3$): 0.22 (s, 6); 0.96 (s, 9); 1.32 (s, 6); 2.74 (s, 1); 2.86 (dd, 1, J=18 and 9 Hz); 2.92 (d, 1, J=2.7 Hz); 3.14 (dd, 1, J=18 and 4 Hz); 3.60 (s, 2); 3.88 (ddd, 1, J=9, 4 and 2.7 Hz); 5.30 (s, 2); 7.54 (d, 2, J=9 Hz); 8.28 (d, 2, J=9 Hz).

(b)

2-oxo-3-(trans)-(1-hydroxy-1-methylethyl)azetidine-4-yl-(2-oxo)butyric-acid.4-nitrobenzylether To an ice-cold solution of 1.4 g of 1-tert.butyldimethylsilyl-2-oxo-3-(trans)-(1-hydroxy-1-methylethyl)azetidine-4-yl-(2-oxo)butyric-acid.4-nitrobenzylether in 60 ml of methanol/water (9/1) are added 2 ml of conc. HCl. This mixture is stirred for 30 minutes at 0° and 5½ hours at 25°. Working-up is analogous to (B)(e).

NMR (CDCl$_3$): 1.26 (s, 3); 1.35 (s, 3); 2.82 (d, 1, J=2.7 Hz); 2.86 (dd, 1, J=19 and 8.6 Hz); 3.06 (dd, 1, J=19 and 5 Hz); 3.60 (s, 2); 3.96 (ddd, 1, J=8.6, 5 and 2.7 Hz); 5.28 (s, 2); 6.37 (br, 1); 7.57 (d, 2, J=9 Hz); 8.27 (d, 2, J=9 Hz).

(c)

3-(1-hydroxy-1-methylethyl)-2-oxoazetidine-4-yl-(2-oxo-3-diazo)butyric-acid.4-nitrobenzylester To an ice cold solution of 0.45 g of 2-oxo-3-(trans)-(1-hydroxy-1-methylethyl)azetidine-4-yl-(2-oxo)butyric-acid.4-nitrobenzylester and 0.33 g of 4-carboxybenzenesulphonylazide in 30 ml of acetonitrile are added 0.67 ml of triethylamine. The remaining procedure is analogous to (B)(i).

NMR (CDCl$_3$): 1.30 (s, 3); 1.38 (s, 3) 2.94 (d, 1, J=2.2 Hz); 3.08 (dd, 1, J=18 and 8.8 Hz); 3.37 (dd, 1, J=18 and 5 Hz); 3.98 (ddd, 1, J=8.8, 5 and 2.2 Hz); 5.38 (s, 2); 6.10 (br, 1); 7.56 (d, 2, J=9 Hz); 8.30 (d, 2, J=9 Hz).

(d)

(5RS,6SR)-1-aza-3,7-dioxo-6-(1-hydroxy-1-methylethyl)bicyclo[3.2.0]heptane-2-carboxylic acid.4-nitrobenzylester A suspension of 0.4 g of 3-(1-hydroxy-1-methylethyl)-2-oxoazetidine-4-yl(2-oxo-3-diazo)butyric-acid.4-nitrobenzylester and 40 mg of rhodium(II)-acetate in 250 ml of abs. benzene is heated for 10 minutes under argon. The remaining procedure is analogous to (B)(j).

NMR (CDCl$_3$): 1.40 (s, 3); 1.46 (s, 3); 2.49 (dd, 1, J=19 and 7.6 Hz); 2.92 (dd, 1, J=19 and 7.2 Hz); 3.26 (d, 1, J=2 Hz); 4.16 (td, 1, J=7.4 and 2 Hz); 4.60 (s, 1); 5.28 (d, 1, J=13.5 Hz); 5.34 (d, 1, J=13.5 Hz); 7.46 (d, 2, J=9 Hz); 8.28 (d, 2, J=9 Hz).

(e)

(5RS,6RS)-1-aza-3,7-dioxo-6-(1-fluoro-1-methylethyl)-bicyclo[3.2.0]heptane-2-carboxylic acid.4-nitrobenzylester To a −78° cold solution of 0.3 ml of diethylaminosulphurtrifluoride and 170 mg of potassium fluoride in 8 ml of dichloromethane is added a solution of 0.35 g of (5RS,6RS)-1-aza-3,7-dioxo-6-(1-hydroxy-1-methylethyl)bicyclo[3.2.0]-heptane-2-carboxylic acid. 4-nitrobenzylester in 17 ml of abs. dichloromethane. The mixture is stirred for 15 minutes at −78° and then mixed with water. The remaining procedure is analogous to (B)(f) m.p. 132°–135°.

NMR (CDCl$_3$): 1.51 (d, 3, J=21 Hz); 1.58 (d, 3, J=21 Hz); 2.56 (dd, 1, J=18.4 and 7.5 Hz); 2.84 (dd, 1, J=18 and 6.7 Hz); 3.36 (dd, 1, J=21 and 2.2 Hz); 4.07–4.31 (m, 1); 4.78 (s, 1); 5.24 (d, 1, J=9.5 Hz); 5.40 (d, 1, J=9.5 Hz); 7.58 (d, 2, J=9 Hz); 8.23 (d, 2, J=9 Hz).

(D)

[(3RS,4RS)-3-(3-(1-fluoro-1-methylethyl)-2-oxoazetidine-4-yl]-(2-oxo)butyric-acid.4-nitrobenzylester (reaction scheme 2, (b)(i), (c)(i)

(a)

(3RS,4RS)-1-tert.butyldimethylsilyl-3-(1-fluoro-1-methylethyl)-2-oxoazetidine-4-yl-(2-oxo)butyric-acid.4-nitrobenzylester To a −78° cold solution of 14.4 ml of dimethylaminosulphurtrifluoride and 18 g of potassium fluoride in 500 ml of dichloromethane is added a solution of 18 g of (3SR,4RS)-1-tert.butyldimethylsilyl-3-(1-hydroxy-1-methylethyl)-2-oxoazetidine-4-yl-(2-oxo)-butyric-acid.4-nitrobenzylester in 400 ml of dichloromethane. Further procedure is as (B)(f) (eluant dichloromethane/ethylacetate=20/1).

IR (CH$_2$Cl$_2$): 1740, 1520 cm$^{-1}$.

(b)

[(3RS,4RS)-3-(1-fluoro-1-methylethyl)-2-oxoazetidine-4-yl]-(2-oxo)butyric-acid.4-nitrobenzylester To an ice cold solution of 5.8 g of (3RS,4RS)-1-tert.butyldimethylsilyl-3-(1-fluoro-1-methylethyl)-2-oxoazetidine-4-yl-(2-oxo)butyric-acid.4-nitrobenzylester in 250 ml of methanol/water (9/1) are added 8.3 ml of conc. HCl. This mixture if stirred for 30 minutes at 0° and 5 hours at 25°. The methanol is removed by distillation and the product crystallized.

(E)

(5RS,6SR)-3-(2-acetylaminoethylthio)-1-aza-6-(1-hydroxy-1-methylethyl)-7-oxobicyclo[3.2.0]hept-2-ene-2-carboxylic acid.4-nitrobenzylester (for example 3)

To an ice-cold solution of 300 mg of (5RS,6SR)-1-aza-3,7-dioxo-6-(1-hydroxy-1-methylethyl)bicyclo[3.2.0]heptane-2-carboxylic acid.4-nitrobenzylester in 20 ml of abs. acetonitrile are added 0.22 ml of N-ethyldiisopropylamine followed by 0.26 ml of phosphoric acid diphenyl ester chloride. After 15 minutes of 0° of a further 0.22 ml of N-ethyldiisopropylamine are added followed by 140 mg of N-acetylcysteamine in 5 ml of abs. acetonitrile. Stirring is continued for 1 hour at 0° and the reaction mixture partitioned between ethylacetate and saturated NaCl. The organic phase is dried over MgSO$_4$ evaporated to dryness and the residue chromatographed over silica gel (ethylacetate/acetone=7/3).

NMR (CDCl$_3$): 1.36 (s, 3); 1.44 (s, 3); 2.00 (s, 3); 2.86–3.64 (m, 7); 4.28 (td, 1, J=9 and 2.7 Hz); 5.25 (d, 1, J=13.5 Hz); 5.56 (d, 1, J=13.5 Hz); 5.92 (br, 1); 7.68 (d, 2, J=9 Hz); 8.26 (d, 2, J=9 Hz).

(F)

(5R,6R)-1-aza-3,7-dioxo-6-[1(S)-fluorethyl]bicyclo[3.2.0]heptane-2-carboxylic acid.4-nitrobenzylester (for examples 23 and 24)

(a)

6(R)-[1-(S)fluoroethyl]penicillanic acid methylester

To a suspension of 6.15 g of potassium fluoride in 200 ml abs. dichloromethane are added at −78° and under argon 10 ml of diethylaminosulphur trifluoride. To this suspension is then added at −78° a solution of 12.5 g of 6-trans-[1-(R)hydroxyethyl]penicillanic acid methylester. After 45 minutes at −78° the cool-bath is removed and stirred continued for 1 hour at room temperature. The reaction mixture is extracted twice with water, dried over MgSO$_4$ and concentrated. The residue is chromatographed on silica gel (dichloromethane) to yield the oily title compound.

NMR (CDCl$_3$): 1.48 (s, 3); 1.54 (dd, 3, J=23.5 and 6.5 Hz); 1.65 (s, 3); 3.55 (ddd, 1, J=28, 3.5 and 2 Hz); 3.79 (s, 3); 4.52 (s, 1); 5.03 (ddq, 1, J=49, 6.5 and 3.5 Hz); 5.55 (d, 1, J=2 Hz).

IR (CHCl$_3$): 1770, 1750 cm$^{-1}$.

(b)

(3R)-4-acetoxy-3-[1(S)-fluorethyl]-1-(3-methyl-2-ene-butyricacidmethylester-2-yl)-2-oxoazetidine To a solution of 7.1 g 6(R)-[1-(S)-fluorethyl]penicillanic acid methylester in 200 ml of ethylacetate are added 21.7 g of mercuric acetate and stirring carried out for 1 hour at 100°. After cooling the mixture is filtered, evaporated to dryness and evaporated three times with toluene. The residue is taken up in ethylacetate and the insoluble part filtered off. The filtrate is washed three times with 400 ml of water dried over MgSO$_4$ and concentrated. The title compound crystallises. m.p. 94°–97°.

IR(CHCl$_3$): 1770, 1720 cm$^{-1}$.

(c)

isopropylidene-[3(R)-(1-(S)fluorethyl)-4(R)-[2-(4-nitrobenzyloxycarbonylmethyl)allyl]-2-oxoazetidine-1-yl]acetic acid methylester To a solution of 6.5 g of (3R)-4-acetoxy-3-[1(S)-fluorethyl]-1-(3-methyl-2-ene-butyric acid methylester-2-yl)-2-oxoazetidine and 8.77 g of 3-methylene-4-trimethylsilylbutyric acid.4-nitrobenzylester (prepared according to K.ITOH et. al., Chem. Comm. 1977, 500) in 30 ml of nitromethane are added at −20° under argon and slowly 9.2 ml of trimethylsilyltriflate. After 15 minutes at −20° the cool bath is removed and stirring continued for 2 hours at room temperature.

The mixture is diluted with 100 ml of ethylacetate, extracted with buffer solution (pH 7) dried over MgSO$_4$ and evaporated to dryness. Chromatography over silica gel (dichloromethane/ether=10/1) yields the oily title product.

NMR (CDCl$_3$): 1.54 (dd, 3, J=24 and 7 Hz); 1.94 (s, 3); 2.20 (s, 3); 2.4 (dd, 1, J=15 and 8.5 Hz); 2.56 (dd, 1, J=15 and 5.5 Hz); 3.13 (ddd, 1, J=24.5, 5.5 and 2.5 Hz); 3.14 (s, 2); 3.74 (s, 3); 4.17 (ddd, 1, J=8.5, 5.5 and 2.5 Hz); 4.98 (dm, 1, J=48 Hz); 5.02 (m, 2 ); 5.22 (s, 2); 7.52 (d, 2, J=9 Hz); 8.22 (d, 2, J=9 Hz).

IR (CHCl$_3$): 1750 cm$^{-1}$.

(d)

4-[3(R)-(1(S)fluorethyl)-2-oxoazetidine-4(R)-yl]-3-oxobutyric-acid.4-nitrobenzylester:

Ozone is passed through a solution of 850 mg of isopropylidene-[3(R)-(1-(S)fluorethyl)-4(R)-[2-(4-nitrobenzyloxycarbonylmethyl)allyl]-2-oxoazetidine-1-yl]acetic acid methylester in 10 ml of dichloromethane at −78° until the solution turns blue. Nitrogen is then added until colour is removed. After addition of 1 ml of dimethylsulfide the mixture is warmed to room temperature and stirred for 2 hours. Dichloromethane is removed and the residue dissolved in 5 ml of methanol and after addition of 1 drop of triethylamine stirred for 30 minutes. After removal of the solvent the residue is mixed with 200 ml of ether, extracted three times with water, dried over MgSO₄ and concentrated. Chromatography over silica gel yields the oily title product.

NMR (CDCl₃): 1.52 (dd, 3, J=24.5 and 7 Hz); 2.86–3.06 (m, 2); 3.07 (ddd, 1, J=27, 3.5 and 2.7 Hz); 3.60 (s, 2); 40.1 (ddd, 1, J=7.5, 6.5 and 2.7 Hz); 5.04 (dm, 1, J=46 Hz); 5.30 (s, 2); 6.08 (br, 1); 7.56 (d, 2, J=9 Hz); 8.29 (d, 2, J=9 Hz).

(e)

4-[3(R)-(1-(S)fluorethyl)-2-oxoazetidine-4(R)-yl]-3-oxo-2-diazobutyricacid.4-nitrobenzylester To a solution of 100 mg of 4-[3(R)-(1-(S)fluorethyl)-2-oxoazetidine-4(R)-yl]-3-oxobutyric-acid.4-nitrobenzylester and 77 mg of 4-carboxybenzenesulphonylazide in 5 ml of acetonitrile are added dropwise under stirring and ice-cooling 0.31 ml of triethylamine and stirring then continued for 15 minutes at room temperature. The mixture is then diluted with 40 ml of ethylacetate, washed once with 5% bicarbonate solution and twice with water, dried over MgSO₄ and concentrated to obtain the title compound.

NMR (CDCl₃): 1.52 (dd, 3, J=24.5 and 7 Hz); 3.10 (dm, 1, J=25 Hz); 3.17 (dd, 1, J=18 and 8.5 Hz); 3.33 (dd, 1, J=18 and 5 Hz); 4.02 (ddd, 1, J=8.5, 5 and 2.5 Hz); 5.03 (dm, 1, J=48.5 Hz); 5.39 (s, 2); 6.04 (br, 1); 7.58 (d, 2, J=9 Hz); 8.30 (d, 2, J=9 Hz).

IR (CH₂Cl₂): 2150, 1770, 1720, 1675 cm⁻¹.

(f)

(5R,6R)-1-aza-3,7-dioxo-6-[1(S)-fluorethyl]bicyclo[3.2.0]heptane-2-carboxylicacid.4-nitrobenzylester A solution of 100 mg of 4-[3(R)-(1-(S)fluorethyl)-2-oxoazetidine-4(R)-yl]-3-oxo-2-diazobutyric-acid.4-nitrobenzylester in 20 ml of benzene is de-gassified by the vigorous passage of argon for 15 minutes with stirring. A catalytic quantity of rhodium(II)-acetate is added and the reaction vessel placed in a prewarmed 80° bath. After 15 minutes at 80° filtration is carried out and the filtrate concentrated to give the title product.

NMR (CDCl₃): 1.59 (dd, 3, J=24 and 7 Hz); 2.50 (dd, 1, J=18 and 8 Hz); 2.94 (dd, 1, J=18 and 7 Hz); 3.48 (ddd, 1, J=26, 4 and 2.5 Hz); 4.22 (td, 1, J=7 and 2.5 Hz); 4.10–4.92 (m, 0.5); 4.80 (s, 1); 5.16–5.50 (m, 2.5); 7.56 (d, 2, J=9 Hz); 8.30 (d, 2, J=9 Hz).

(G)

N,N,N',N'-tetramethyl-N''-(2-mercapto)ethylguanidine.Hydroiodide (for example 10)

(a)

N,N,N',N'-tetramethyl-S-methylisothioureiciodide

To 100 ml of methyliodide and 200 ml of dichloromethane are added with ice-cooling 30 g of tetramethylthiourea and the mixture then stirred for 3 hours in darkness and at room temperature. After the addition of 500 ml of ether the precipitated title compound (m.p. 170°) can be directly further reacted.

(b)

N,N,N',N'-tetramethyl-N''-(2-mercapto)ethylguanidine.Hydroiodide

A solution of 2.27 g of cysteamine HCl in 20 ml of abs. dimethylformamide is mixed at room temperature with 2.77 ml of triethylamine and stirred for 2 hours. The precipitate is removed and the filtrate mixed with 5.48 g of N,N,N',N'-tetramethyl-S-methylisothioureiciodide. After two hours of stirring at room temperature the mixture is mixed with 100 ml of diisopropylether and decanted from the resulting brown oil. This oil is digested with 10 ml of isopropanol whereupon the title compound crystallises. After filtration the residue is washed once with isopropanol and once with diisopropylether and dried to yield the title compound of m.p. 95°.

NMR (CDCl₃): 2.10 (br, 1); 2.90–3.30 (m, 14); 3.42–3.70 (m,2); 7.66 (br, 1).

IR (KBr): 1615, 1580 cm⁻¹.

(H)

N,N,N'-trimethylmercaptoacetamidine.Nonafluorobutanesulfonate (for example 12)

(a)

α-tritylthio-N-methylacetamide

To a solution of 26.55 g of sodium in 1800 ml of ethanol is added 288.8 g of tritylmercaptan. Then with ice-cooling a solution of 111.8 g of N-methylchloracetamide in 1000 ml of ethanol is added dropwise whereupon a grey-white precipitate is formed. After completion of the addition stirring is continued at room temperature for 45 minutes and the mixture then concentrated to half its volume. The precipitate is filtered, washed with isopropanol, water and again isopropanol and dried to give the title product. m.p. 200°–210°.

NMR (CDCl₃): 2.48 (d, 3, J=5.5 Hz); 3.13 (s, 2); 6.00 (br, 1); 7.10–7.60 (m, 15).

(b)

α-tritylthio-N-methylthioacetamide 325 g of α-tritylthio-N-methylacetamide und 400 g Lawesson-Reagent are stirred for 6 hours in 4000 ml of toluene at 50°. After concentration to ca. 1300 ml the insoluble matter is removed and the residue washed with ethylacetate. The original filtrate and the ethyl acetate phase are combined and evaporated to dryness. The oily residue is made to crystalise by digestion with a little ethanol to give the title product more of which can be obtained by chromatography of the mother liquor over silica gel.

NMR (CDCl₃): 2.75 (d, 3, J=5.5 Hz); 3.85 (s, 2); 7.20–7.60 (m, 15); 7.90 (br, 1).

IR (KBr): 1520, 1440, 1360 cm⁻¹.

(c)

α-tritylthio-N,S-dimethylacetic acid imidothioester.Hydroiodide 136 g of α-tritylthio-N-methylthioacetamide are stirred in darkness for 20 hours at room temperature in 800 ml of methyliodide. 1500 ml of ethylacetate are then added and the mixture filtered and washed through twice with ethylacetate to yield the title product. m.p. 130°–140°.

NMR (C₂D₂Cl₄): 2.20 (s, 3); 3.08 (s, 3); 3.77 (s, 2); 7.20–7.60 (m, 15).

IR (KBr): 1600 cm⁻¹.

(d)

α-tritylthio-N,N,N'-trimethylacetamidine.Hydroiodide

Dimethylamine is condensed over a dry-ice cooler into a suspension of 170 g of 60 -tritylthio-N,S-dimethylacetic acid imidothio ester.hydroiodide in 750 ml of abs.dichloromethane with stirring at room temperature (ca. 200 ml) and the by then clear solution stirred for a further 3 hours at room temperature. Evaporation to dryness is carried out and the residue brought to crystallisation by digestion with ethylacetate. Filtration and drying yield the title product. m.p. 190°.

NMR ($C_2D_2Cl_4$): 2.80–3.06 (m, 9); 3.32 (s, 2); 7.25–7.60 (m, 15); 8.58 (br, 1).

IR (KBr): 1640 cm$^{-1}$.

(e)

N,N,N'-trimethylmercaptoacetamidine.Nonafluorobutanesulfonate 10 g of α-tritylthio-N,N,N'-trimethylacetamidinehydroiodide are partitioned between 6N NaOH and ether to yield the free base and then dissolved in 100 ml of methanol. At the same time a solution of 4.2 g of silver nitrite in 500 ml of methanol and 2.5 ml of pyridine is prepared. The solutions are combined and stirred for 90 minutes at room temperature. The resulting black-brown precipitate is filtered and washed through with methanol and ether. It is then suspended in 400 ml abs. dichloromethane to which is added 1 drop of pyridine and then for ca. 20 minutes at 0° $H_2S$. After filtration through a glass frit the filtrate is concentrated, mixed with toluene and again evaporated to dryness. Following high-vacuum drying the residue is taken up in ca. 100 ml of 1N HCl and extracted three times with ethylacetate. 10 g of solid potassium nonafluorobutane sulphonate are added and the mixture extracted 5 times with dichloromethane. After concentration of the combined extracts the title product crystallines out. m.p. 60°–65° (decomp.).

NMR (CDCl$_3$): 2.42 (br, 1); 3.10–3.26 (m, 6); 3.37 (s, 3); 3.64 (br, 2); 8.04 (br, 1).

IR (KBr): 1650 cm$^{-1}$.

We claims:

1. A compound of the formula

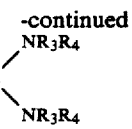

(I)

wherein

R$_1$ is hydrogen or methyl, and

R$_2$ is a substituent of the formula

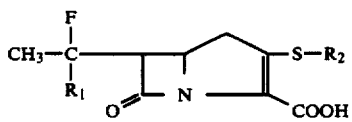

(II)

or

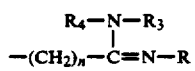

(IIa)

wherein

R$_4$, R$_5$ and R$_6$ are the same or different and are hydrogen or lower alkyl or R$_4$ and R$_5$ are joined to form a ring in II and IIa, which rings are unsubstituted or mono- or poly-substituted by alkyl, hydroxy, carboxy or di-(lower)-alkylamino, m is 2 or 3, and n is 1, 2 or 3 or a salt thereof or a zwitterion thereof, with the proviso that when R$_1$ is hydrogen and the group containing it has R- configuration, R$_2$ is not acetylaminoethyl.

2. A compound according to claim 1 selected from the group consisting of

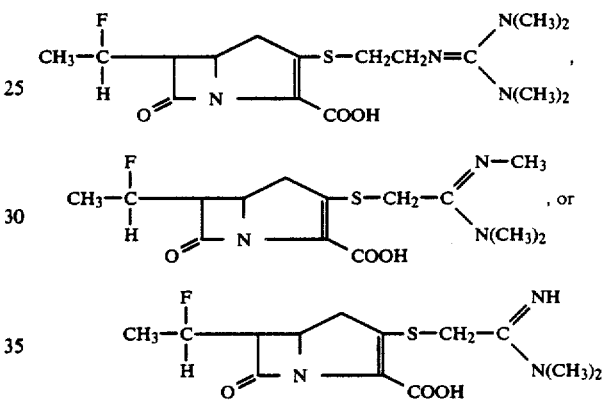

or a protected form thereof and/or a physiologically-hydrolyzable and acceptable ester thereof, or a salt thereof or a zwitterion thereof.

3. An antimicrobial composition comprising an effective amount of a compound as claimed in claim 1 or a pharmaceutically acceptable salt or zwitterion thereof together with a pharmaceutically acceptable diluent or carrier.

4. An antimicrobial composition comprising an effective amount of a compound as claimed in claim 2 or a pharmaceutically acceptable salt or zwitterion thereof together with a pharmaceutically acceptable diluent or carrier.

5. A method of combating bacteria which comprises administering to a subject in need of such treatment an effective amount of a compound as claimed in claim 1 or a pharmaceutically acceptable salt or zwitterion thereof together with a pharmaceutically acceptable diluent or carrier.

6. A method of combating bacteria which comprises administering to a subject in need of such treatment an effective amount of a compound as claimed in claim 2 or a pharmaceutically acceptable salt or zwitterion thereof together with a pharmaceutically acceptable diluent or carrier.

* * * * *

UNITED STATES PATENT AND TRADEMARK OFFICE
CERTIFICATE OF CORRECTION

PATENT NO. : 4,720,490

DATED : January 19, 1988

INVENTOR(S) : Ching P. MAK et al.

It is certified that error appears in the above-identified patent and that said Letters Patent is hereby corrected as shown below:

ON THE TITLE PAGE:

In the Assignee Data, that portion reading "Sandoz Ltd." should read --Sanraku Incorporated--.

Signed and Sealed this

Fifth Day of July, 1988

*Attest:*

DONALD J. QUIGG

*Attesting Officer*  *Commissioner of Patents and Trademarks*